US00PP26549P2

(12) United States Plant Patent
Wood

(10) Patent No.: US PP26,549 P2
(45) Date of Patent: Mar. 29, 2016

(54) LILAC PLANT NAME 'SMSJBP7'

(50) Latin Name: *Syringa hybrida*
Varietal Denomination: SMSJBP7

(71) Applicant: Timothy D. Wood, Spring Lake, MI (US)

(72) Inventor: Timothy D. Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 145 days.

(21) Appl. No.: 13/987,989

(22) Filed: Sep. 20, 2013

(51) Int. Cl.
*A01H 5/02* (2006.01)

(52) U.S. Cl.
USPC ..... Plt./248

(58) Field of Classification Search
USPC ..... Plt./248
See application file for complete search history.

(56) References Cited

PUBLICATIONS

Spring Meadow Nursery, Flowering Shrubs Spring Meadow Nursery, Inc. Starter Plants Catalog and Shrub Reference 2012-2013, pp. 1-3, 9, 17 and 69.*

* cited by examiner

*Primary Examiner* — June Hwu
(74) *Attorney, Agent, or Firm* — C. A. Whealy

(57) ABSTRACT

A new and distinct cultivar of Lilac plant named 'SMSJBP7', characterized by its upright and somewhat outwardly spreading plant habit; vigorous growth habit; freely branching habit; freely flowering habit; dark purple-colored flower buds; large inflorescences with fragrant dark lavender purple-colored flowers; long flowering period and remontant flowering habit; and good cold hardiness.

2 Drawing Sheets

Botanical designation: *Syringa hybrida.*
Cultivar denomination: 'SMSJBP7'.

BACKGROUND OF THE INVENTION

The present invention relates to a new and distinct cultivar of Lilac plant, botanically known as *Syringa hybrida* and hereinafter referred to by the name 'SMSJBP7'.

The new Lilac plant is a product of a planned breeding program conducted by the Inventor in Grand Haven, Mich. The objective of the breeding program is to create new compact Lilac plants with repeat flowering habit and unique flower colors.

The new Lilac plant originated from an open-pollination during the spring of 2006 of *Syringa hybrida* 'Penda', disclosed in U.S. Plant Pat. No. 20,575, as the female, or seed, parent with an unknown proprietary selection of *Syringa hybrida* as the male, or pollen, parent. The new Lilac plant was discovered and selected by the Inventor as a single flowering plant from within the progeny of the stated open-pollination in a controlled environment in Grand Haven, Mich. during the spring of 2010.

Asexual reproduction of the new Lilac plant by softwood cuttings in a controlled greenhouse environment in Grand Haven, Mich. since the spring of 2010 has shown that the unique features of this new Lilac plant are stable and reproduced true to type in successive generations of asexual reproduction.

SUMMARY OF THE INVENTION

Plants of the new Lilac have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMSJBP7'. These characteristics in combination distinguish 'SMSJBP7' as a new and distinct Lilac plant:

1. Upright and somewhat outwardly spreading plant habit.
2. Vigorous growth habit.
3. Freely branching habit.
4. Freely flowering habit.
5. Dark purple-colored flower buds.
6. Large inflorescences with fragrant dark lavender purple-colored flowers.
7. Long flowering period and remontant flowering habit.
8. Good cold hardiness.

Plants of the new Lilac can be compared to plants of the female parent, 'Penda'. Plants of the new Lilac differ primarily from plants of 'Penda' in the following characteristics:

1. Plants of the new Lilac are larger and more vigorous than plants of 'Penda'.
2. Plants of the new Lilac have darker-colored flower buds than plants of 'Penda'.
3. Plants of the new Lilac have larger inflorescences than plants of 'Penda'.
4. Plants of the new Lilac have a stronger remontant flowering habit than plants of 'Penda'.

Plants of the new Lilac can be also compared to plants of the *Syringa hybrida* 'SMSXPM', disclosed in U.S. plant patent application Ser. No. 13/987,979. In side-by-side comparisons conducted in Grand Haven, Mich., plants of the new Lilac differed primarily from plants of 'SMSXPM' in the following characteristics:

1. Plants of the new Lilac were more upright than and not as outwardly spreading plants of 'SMSXPM'.
2. Flowers of plants of the new Lilac were not as fragrant as flowers of plants of 'SMSXPM'.
3. Flowers of plants of the new Lilac and 'SMSXPM' differed in flower bud and flower color as plants of 'SMSXPM' had dark pink-colored flower buds and light pink-colored flowers.

BRIEF DESCRIPTION OF THE PHOTOGRAPHS

The accompanying colored photographs illustrate the overall appearance of the new Lilac plant showing the colors as true as it is reasonably possible to obtain in colored reproductions of this type. Colors in the photographs may differ slightly from the color values cited in the detailed botanical description which accurately describe the colors of the new Lilac plant.

The photograph on the first sheet is a side perspective view of a flowering typical plant of 'SMSJBP7' grown in an outdoor nursery.

The photograph on the second sheet is a close-up view of a typical flowering plant of 'SMSJBP7'.

DETAILED BOTANICAL DESCRIPTION

The aforementioned photographs and following observations, measurements and values describe plants grown during the spring and summer in an outdoor nursery in Grand Haven, Mich. and under cultural practices typical of commercial production. Plants were four years old when the photographs and the description were taken. In the description, color references are made to The Royal Horticultural Society Colour Chart, 1995 Edition, except where general terms of ordinary dictionary significance are used.

Botanical classification: *Syringa hybrida* 'SMSJBP7'.

Parentage:

*Female, or seed, parent.*—*Syringa hybrida* 'Penda', disclosed in U.S. Plant Pat. No. 20,575.

*Male, or pollen, parent.*—Unknown proprietary selection of *Syringa hybrida*, not patented.

Propagation:

*Type.*—By softwood cuttings.

*Time to initiate roots, summer.*—About 18 days at 27° C.

*Time to produce a rooted young plant, summer.*—About three months at 27° C.

*Root description.*—Fine, fibrous.

*Rooting habit.*—Freely branching; dense.

Plant description:

*Plant form and growth habit.*—Perennial shrub; upright and somewhat outwardly spreading plant habit; vigorous growth habit.

*Branching habit.*—Freely branching habit, about 27 lateral branches develop per plant.

*Plant height.*—About 92 cm.

*Plant diameter* (*area of spread*): About 85 cm.

Lateral branch description:

*Length.*—About 36 cm.

*Diameter.*—About 2 mm.

*Internode length.*—About 4.2 cm.

*Aspect.*—About 10° to 20° from vertical.

*Texture.*—Smooth, glabrous.

*Color.*—Close to 197A.

Leaf description:

*Arrangement.*—Opposite, simple.

*Length.*—About 4.1 cm.

*Width.*—About 2.5 cm.

*Shape.*—Ovate.

*Apex.*—Acuminate.

*Base.*—Obtuse.

*Margin.*—Entire; slightly undulate and ciliate; no sinuses.

*Texture, upper and lower surfaces.*—Rough, pubescent.

*Venation pattern.*—Pinnate.

*Color.*—Developing and fully expanded leaves, upper surface: Close to 139A; venation, close to 145C. Developing and fully expanded leaves, lower surface: Close to 147B; venation, close to 137B.

*Petioles.*—Length: About 5 mm. Diameter: About 1 mm. Texture, upper and lower surfaces: Pubescent. Color, upper and lower surfaces: Close to 139A.

Flower description:

*Flower arrangement and flowering habit.*—Single salverform flowers arranged and axillary terminal panicles; inflorescences moderately dense to dense and conical in shape; freely flowering habit with usually about 126 flowers developing per inflorescence; flowers face mostly outwardly on inflorescences that may be upright, horizontal or downward depending on the inflorescences' position on the plant.

*Natural flowering season and flower longevity.*—Long flowering period; plants of the new Lilac flower from spring to autumn in Grand Haven, Mich.; remontant flowering habit; flowers last about three to four weeks on the plant; flowers not persistent.

*Fragrance.*—Moderately fragrant; fragrance sweet and pleasant.

*Inflorescence height.*—About 7 cm.

*Inflorescence diameter.*—About 8.5 cm.

*Flower diameter.*—About 1 cm.

*Flower length* (*height*).—About 1 cm.

*Flower buds.*—Length: About 5 mm. Diameter: About 3 mm. Shape: Obovate. Color: Close to 93A.

*Petals.*—Quantity and arrangement: Single whorl of four petals; lower portion of petals fused forming a narrow tube; corolla tube semi-erect to horizontal and occasionally recurved; corolla tube without undulations. Lobe length: About 5 mm. Lobe width: About 2 mm. Corolla tube length: About 1.2 cm to 1.5 cm. Corolla tube diameter: About 2 mm. Lobe shape: Elliptic. Apex: Acute. Margin: Entire; apical margin initially moderately to strongly incurved and becoming flatter with development. Texture, upper and lower surfaces: Smooth, glabrous. Color: When opening, petal lobe upper surface: Close to 83C. When opening, petal lobe lower surface: Close to 83A. Fully opened, petal lobe upper surface: Close to 81B. Fully opened, petal lobe lower surface: Close to 81D. Corolla tube, inner and outer surfaces: Close to 83A to 83C.

*Sepals.*—Quantity and arrangement: Single whorl of three to four sepals; fused towards the base forming a campanulate-shaped calyx. Length: About 4 mm. Width: About 3 mm. Shape: Subulate. Apex: Acute. Margin: Entire. Texture, upper and lower surfaces: Smooth. Color, upper and lower surfaces: Close to 144D.

*Peduncles.*—Length: About 14 cm. Diameter: About 2 mm. Strength: Strong. Aspect: About 40° to 50° from lateral branch axis. Texture: Smooth. Color: Close to 148A.

*Pedicels*.—Length: About 7 mm. Diameter: About 1 mm. Strength: Strong. Aspect: About 45° to 55° from peduncle axis. Texture: Smooth. Color: Close to 148A.

*Reproductive organs*.—Androecium: Quantity of stamens per flower: About four. Anther shape: Narrowly oblong. Anther length: About 3 mm. Anther color: Close to 187B. Amount of pollen: Scarce. Pollen color: Close to 4D. Gynoecium: Pistil length: About 5 mm. Style length: About 3 mm. Style color: Close to 18B. Stigma shape: Round. Stigma color: Close to 18B. Ovary: Close to 148A.

*Fruits*.—Length: About 1.5 cm to 1.8 cm. Diameter: About 3 mm to 4 mm. Texture: Leathery. Color: Initially, close to 156B; with development becoming closer to 166A and eventually closer to 198B.

*Seeds*.—Length: About 1 cm. Diameter: About 2.5 mm. Color: Close to 165A.

Garden performance. Plants of the new Lilac have been observed to have good garden performance and to tolerate rain, wind and temperatures ranging from about −31° C. to about 38° C.

Pathogen & pest resistance: Plants of the new Lilac have been observed to be resistant to root rots common to Lilac plants. Plants of the new Lilac have not been shown to be resistant to pests and other pathogens common to Lilac plants.

It is claimed:

1. A new and distinct Lilac plant named 'SMSJBP7' as illustrated and described.

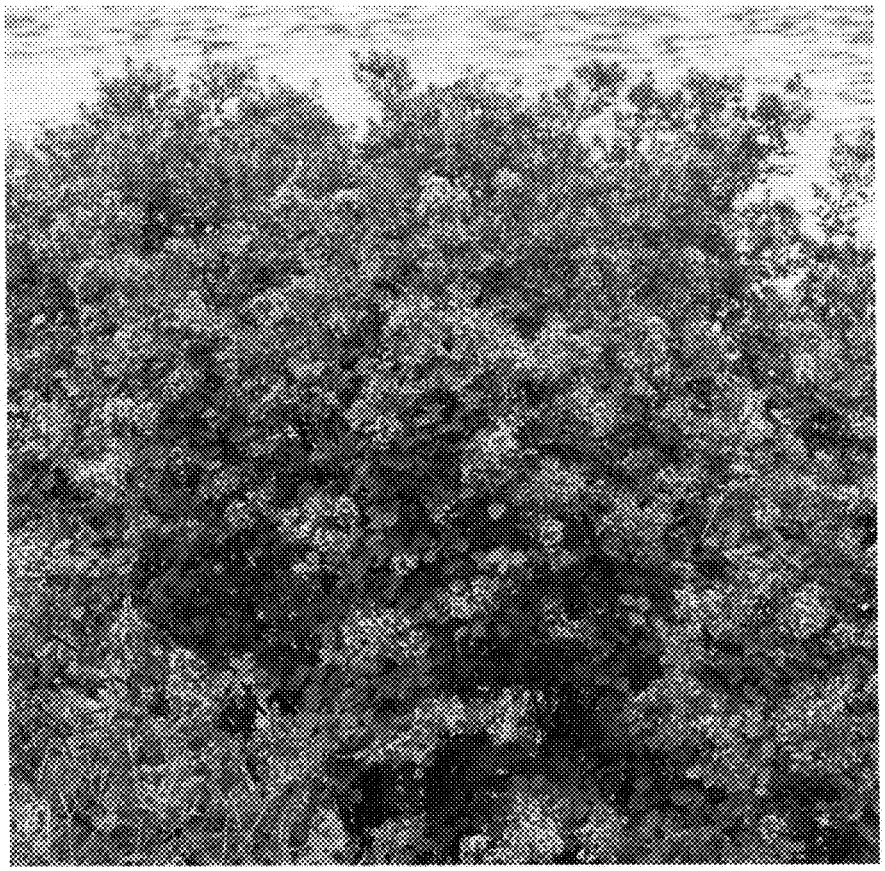

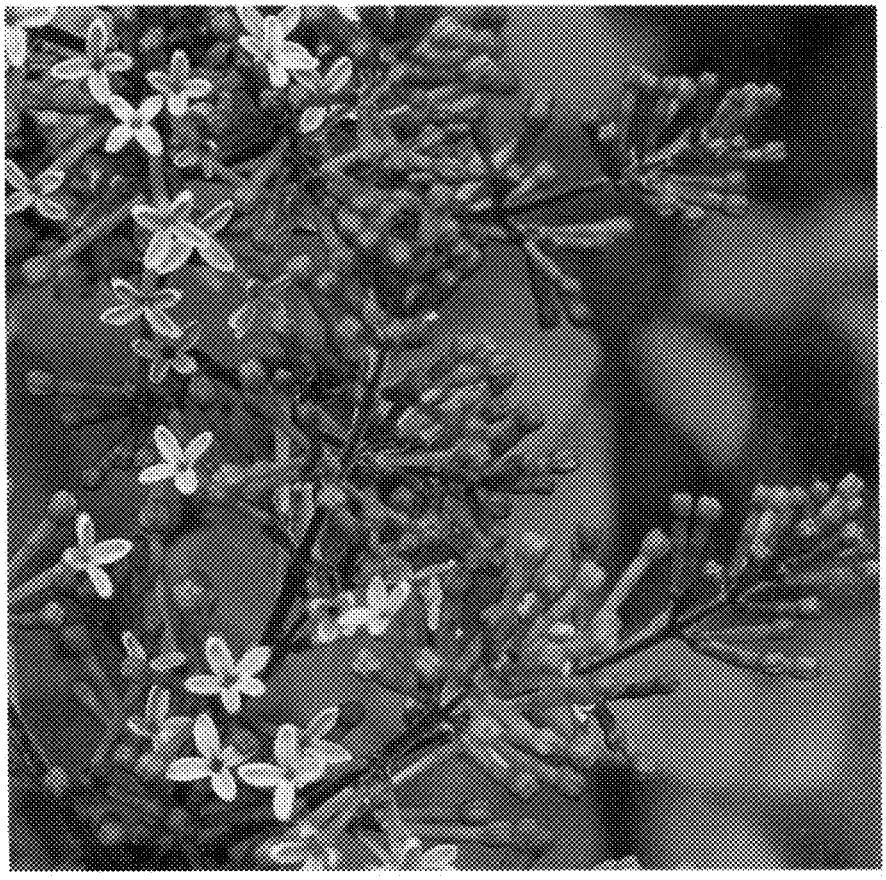

* * * * *